United States Patent [19]

English

[11] Patent Number: 4,895,015
[45] Date of Patent: Jan. 23, 1990

[54] HORIZONTAL PULL SLIPMETER

[76] Inventor: William English, 3018 Hunt Rd., Oakton, Va. 22124

[21] Appl. No.: 317,583

[22] Filed: Mar. 1, 1989

[51] Int. Cl.⁴ .............................................. G01N 19/02
[52] U.S. Cl. .......................................................... 73/9
[58] Field of Search ........................................ 73/9, 10

[56] References Cited

U.S. PATENT DOCUMENTS 4,081,989  4/1978  Majcherezyk ........................ 73/105

OTHER PUBLICATIONS

Standart Test Method for Static Slip Resistance of Footwear Sole, Heel or Related Materials by Horizontal Pull Slipmeter (ASTM), 1984.

Primary Examiner—John Chapman
Assistant Examiner—Michele Simons
Attorney, Agent, or Firm—Norman B. Rainer

[57] ABSTRACT

An improvement in a Horizontal Pull Slipmeter (HPS) enables more accurate and more rapid coefficient of friction measurements to be made upon walking surfaces. The improvement involves a specialized interaction between a drag sled and a stationary pulling mechanism which in conventional HPS devices, are seperate entities. The specialized interaction utilizes paired tracks which extend from the pulling mechanism and serve to guide the drag sled. The pulling mechanism utilizes a motor which is automatically activated when the HPS is placed on the walking surface and pulls the drag sled at a constant speed.

3 Claims, 5 Drawing Sheets

HORIZONTAL PULL SLIPMETER

BACKGROUND OF THE INVENTION

This invention relates to the measurement of coefficients of friction on walking surfaces and more specifically concerns an improvement in a widely used type of instrument known as a Horizontal Pull Slipmeter, hereinafter referred to by the acronym HPS.

The HPS is generally accepted by industrial standards as a device for measuring the coefficient of friction of a walking surface. It was developed by C. H. Irvine of Liberty Mutual Insurance Co. of Hopkinton, Masss., and is described in ASTM Method F:609-79. Its standard construction consists of two basic elements: (a) a drag sled mounted upon slider feet and fitted with a force gage, and (b) means for pulling the sled across the floor surface being tested at a controlled rate of speed. Although the design of the drag sled and force gage are specified in industry standards, the configuration of the pulling means may take any form, provided it serves the specified function. In most applications, a servo-type unit is employed to pull the sled in a horizontal manner across a floor surface by means of a flexible string which is wound onto a wheel driven at a prescribed constant speed by the servo unit.

The HPS has specific attributes that yield advantages over alternative devices for making such measurements. It is portable, simple to use, and self-calibrating. However, the device has certain shortcomings which limit its further acceptance as an industrial standard tester. The HPS will not accurately measure the coefficient of friction (COF) on wet surfaces because it takes too long to set up the two components for testing. By the time both components are placed into position and connected by means of the string, the slider feet of the drag sled have displaced most of the moisture from the surface being tested. Furthermore, the time delay permits the resilient material of the slider feet to begin to conform to the surface microtopography (a phenomena known as the "sticksion problem"). These factors can contribute to artificially high friction readings. In addition, vagaries in the arrangement of pulling means employed in the test may introduce an additonal variable and the possibility of operator-dependent bias in results. For example, even though the wheel which winds the string is driven at a constant speed, the details of alignment are not controlled.

It is therefore an object of the present invention to provide a device capable of taking valid coefficient of friction measurements on wet or dry surfaces.

It is another object to provide a device of the aforesaid nature having no operator-dependent variables.

It is yet another object of the invention to provide a device of the aforesaid nature which is faster and easier to use than the present HPS instrument.

SUMMARY OF THE INVENTION

The above and other beneficial objects and advantages are accomplished in accordance with the present invention by an improvement in a Horizontal Pull Slipmeter having a sled assembly comprised of:
(a) a drag weight having top and bottom surfaces and opposed sides,
(b) downwardly directed slider feet emergent from said bottom surface, and adapted to simultaneously contact a flat surface whose coefficient of friction is to be measured, and
(c) a force gage affixed to said drag weight and having a visual display scale and a forwardly directed activating plunger, said improvement comprised of:
(a) a pair of horizontally disposed elongated parallel guide means having forward and rear extremities and upper and lower retaining shoulders which define facing channels adapted to slidably embrace the opposed sides of said drag weight, permitting said sled assembly horizontally reciprocating unencumbered movement along said guide means,
(b) a servo assembly comprising:
  (1) an outer housing having front, rear, upper and lower surfaces and opposed sides, said housng being attached to the forward extremities of said guide means,
  (2) a direct current electric motor coupled to transmission means having a rearwardly directed threaded output shaft which rotates at a constant speed,
  (3) a propulsion bar coextensive with said output shaft, extending through the rear surface of said housing and terminating in a free rear extremity, said propulsion bar being threadably engaged with said output shaft so as to undergo reciprocal axial motion
  (4) a battery power source of sufficient voltage to energize said motor,
  (5) a rheostat to calibrate the speed of said motor and consequently control said reciprocal movement,
  (6) forward and rear limiting switches adapted to limit the length of stroke of said propulsion bar in said reciprocal movement, and
  (7) a DPDT switch adapted to control the direction of reciprocal movement of said bar,
(c) a linkage having first and second extremities, said first extremity pivotably engaging the free rear extremity of said propulsion bar, said second extremity pivotably engaging the activating plunger of the force gage,
(d) forward and rear lifting means, each comprised of paired opposed upright support arms having upper and lower extremities, said upper extremities associated with handles oriented traversely to the guide means,
(e) four fixed support feet disposed in a substantially rectangular array and adapted to simultaneously rest upon said horizontal surface, and
(f) an activation switch associated with the rear extremity of at least one of said guide means, said switch having a downwardly directed touch rod whose bottom extremity extends lower than said support feet, whereby said touch rod contacts said horizontal surface simultaneously with the slider feet, and the propulsion bar begins forward movement of the sled assembly while the servo assembly and guide means are held stationary.

In preferred embodiments, the support feet are constructed of a resilient non-slip material such as latex rubber.

In another embodiment, a foot pressure means may be affixed forwardly of said servo assembly. Downward pressure may be applied to said pressure means to pivot the HPS away from the floor surface in readiness to descend to perform a measurement.

In a further embodiment, a removeable lockpin may be inserted through apertures in the guide means to secure the drag sled during transport.

The retaining shoulders of the guide means may have a beveled inner surface to center said sled assembly when the device is lifted by the handles.

The sled assembly preferably employs the Chatillon DPP-5 Force Gauge or its equivalent. In alternative embodiments, digital type gauges may be used.

BRIEF DESCRIPTION OF THE DRAWING

For a fuller understanding of the nature and objects of the invention, reference should be had to the following detailed description taken in connection with the accompanying drawing forming a part of this specification and in which similar numerals of reference indicate corresponding parts in all the figures of the drawing.

DESCRIPTION OF THE PREFERRED EMBODIMENT

Figure 1:
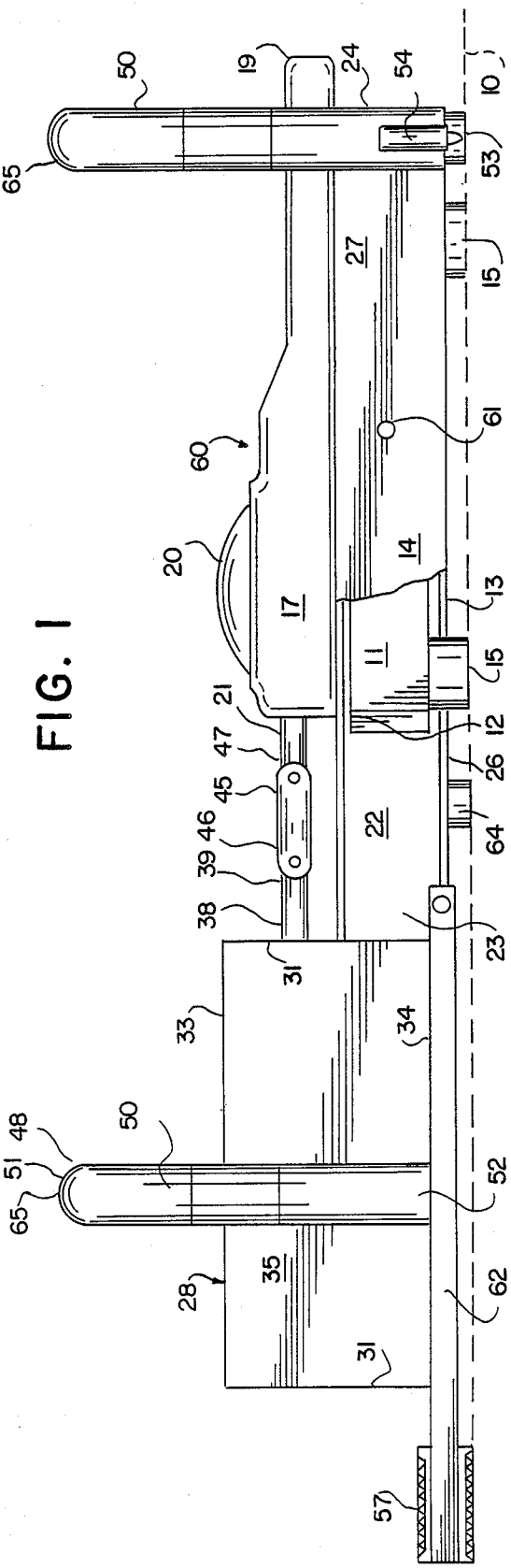
FIG. 1 is a side view, of an embodiment of the improved slipmeter of the present invention with portions cut away to reveal interior details.
Figure 2:
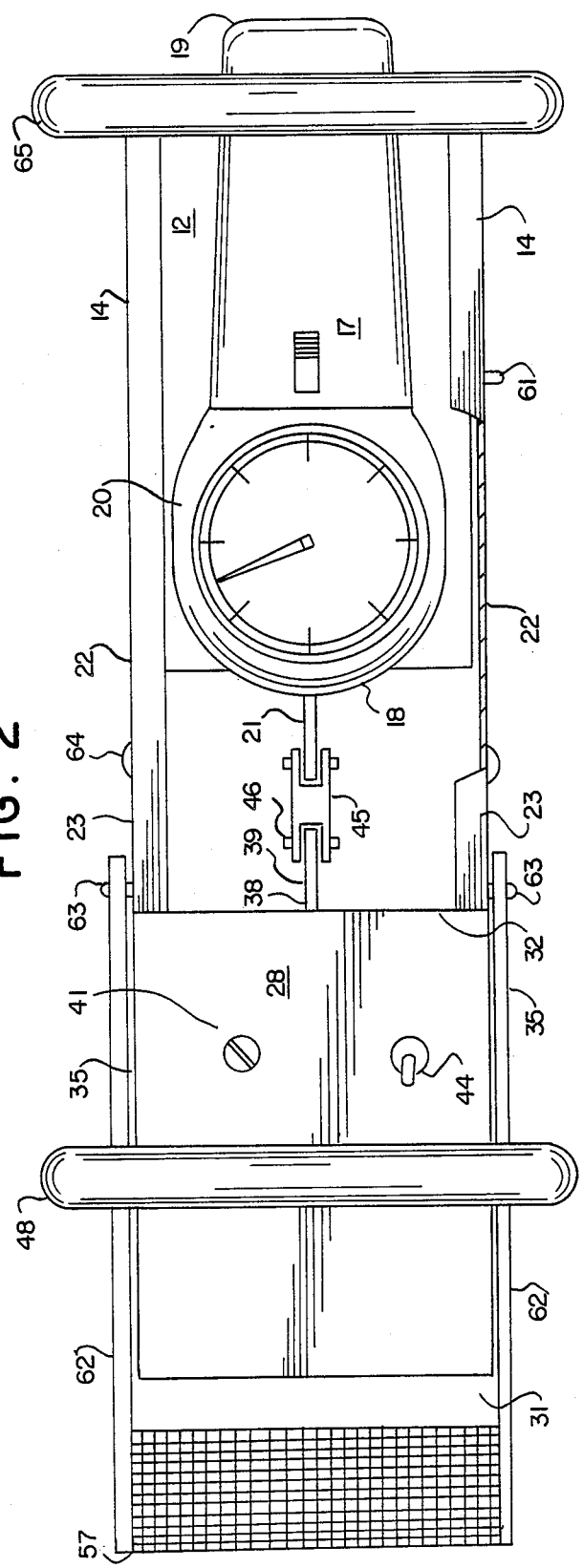
FIG. 2 is a top view of the embodiment of FIG. 1 with portions cut away.
Figure 3:
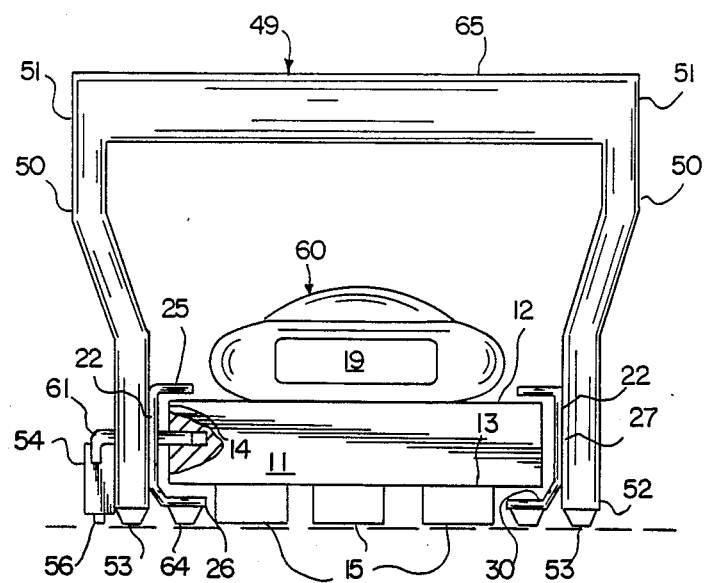
FIG. 3 is a rear view of the embodiment of FIG. 1.

Referring to FIGS. 1-5, an embodiment of the apparatus of the present invention is shown in operative relationship with the conventional sled assembly 60 of a Horizontal Pull Slipmeter adapted for use upon horizontal surface 10. The sled assembly is comprised of drag weight 11 having parallel top and bottom surfaces 12 and 13, respectively, and parallel sides 14. Downwardly directed slider feet 15 are emergent from bottom surface 13, and are adapted to simultaneously contact horizontal surface 10.

Force gage assembly 17 is affixed to top surface 12, and has forward and rear extremities 18 and 19, respectively, and visual display scale 20. A plunger 21 that activates scale 20 is forwardly emergent from forward extremity 18.

The improvement of the present invention is comprised in part of horizontally disposed elongated parallel guide means in the form of paired rails 22, having forward and rear extremities 23 and 24, respectively, and upper and lower retaining shoulders 25 and 26, respectively, which define facing channels 27. As shown more clearly in FIGS. 2 and 3, the channels are adapted to slidably embrace opposite sides 14 of drag weight 11, permitting the drag sled horizontally reciprocating unencumbered movement along rails 22. The forward extremities of the rails are attached to servo assembly 28.

Figure 4:
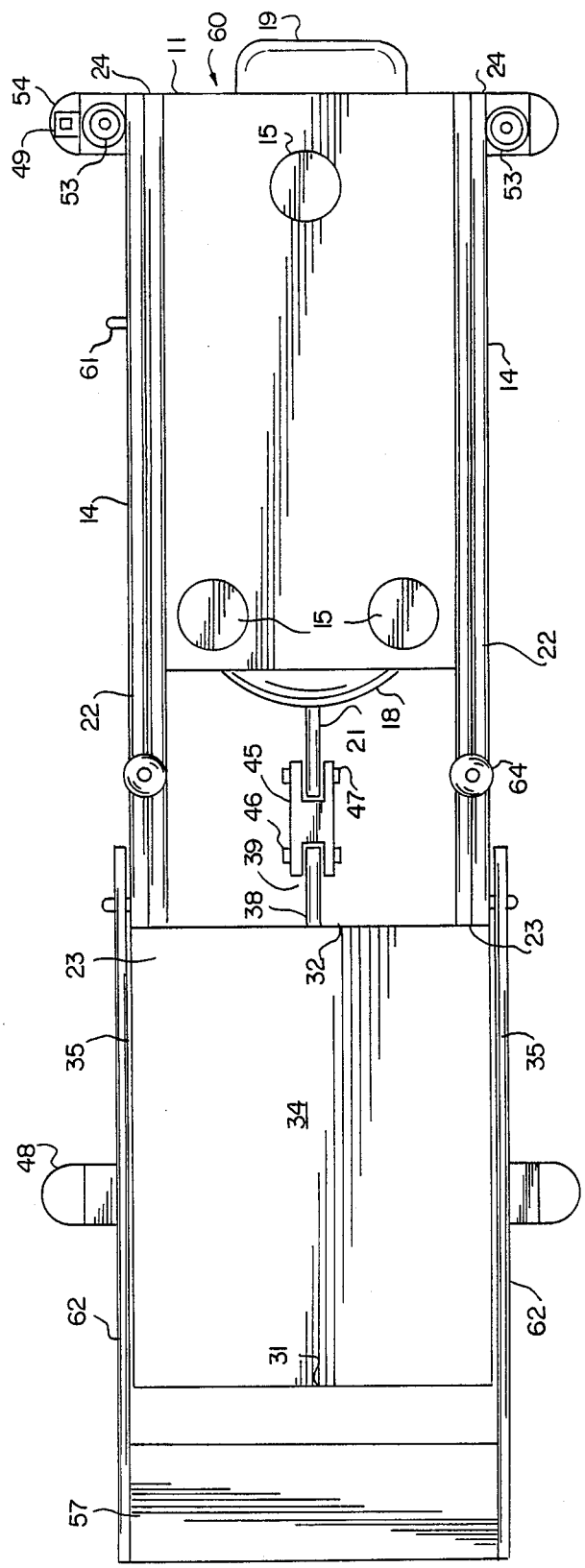
FIG. 4 is a bottom view of the embodiment of FIG. 1.
Figure 5:
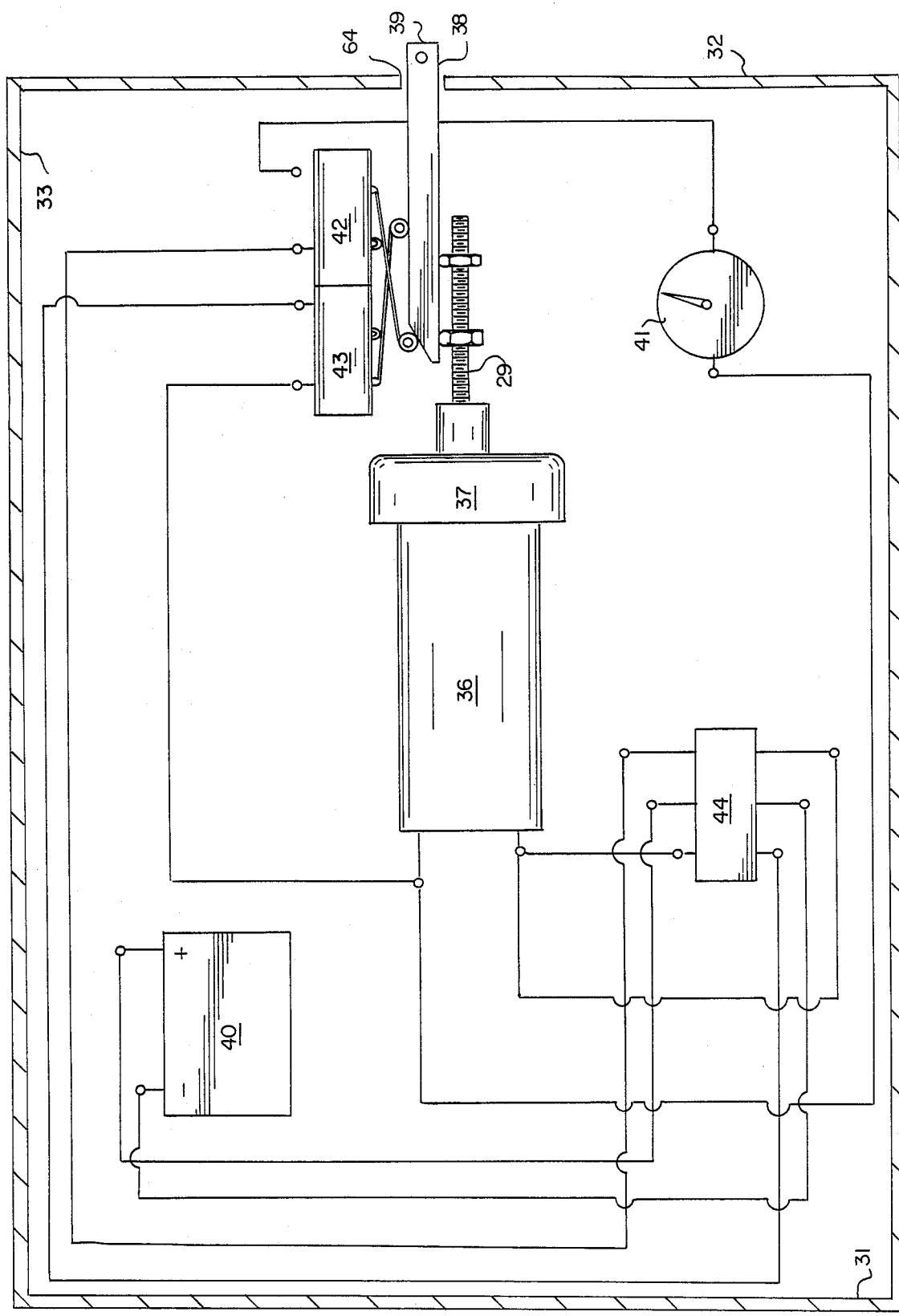
FIG. 5 is a schematic diagram of an embodiment of the servo assembly of the present invention.

As best shown in FIGS. 4 and 5, servo assembly 28 is comprised of a housing having front, rear, upper and lower panels 31, 32, 33 and 34, respectively, and parallel sides 35. The housing confines a direct current electric motor 36 coupled to a speed reducing transmission means 37 having a rearwardly directed threaded output shaft 29. Longitudinally disposed flat propulsion bar 38, having free rear extremity 39 extending through slot 64 in rear panel 32, is adapted to reciprocate axially by virtue of threaded joinder with output shaft 29.

Battery 40, preferably of the rechargeable type, is provided to produce sufficient voltage to energize motor 36 and cause rotation at a specific speed. A rheostat 41 controls the speed of the motor for different test conditions, and consequently controls the reciprocal movement. Normally open forward limiting switch 43 and normally closed rear limit switch 42, are adapted to limit the length of stroke of propulsion bar 38 in its linear movement. DPDT switch 44 is adapted to control the direction of reciprocal movement of the shaft and bar.

A connecting link 45 has a first extremity 46 that pivotably engages rear extremity 39 of propulsion bar 38, and a second extremity 47 that pivotably engages plunger 21 of gage 17.

Lifting means in the form of forward and rear handles 48 and 49, respectively, are each comprised of paired upright support arms 50 having upper extremities 51 and lower extremities 52. The lower extremities of the forward lifting means attach to the sides 35 of said housing. The lower extremities of the rear lifting means attach to said rails. Upper extremities 51 are fixedly associated with handle bars 65 perpendicularly disposed to said rails. Two forward support feet 64 are affixed to the underside of lower retaining shoulders 26. Two rearward support feet 53 are affixed beneath the lower extremities 52 of rear handle 49. The four support feet are disposed in a substantially rectangular array, and are adapted to simultaneously rest upon horizontal surface 10.

Activation switch 54 is associated with lower extremity 52 of one of support arms 50 of rear handle 49. The switch has downwardly directed activating means in the form of touch rod 55 having a bottom extremity 56 extending lower than feet 53 in the open or inactive position and aligned with the feed in the closed or activated position.

Pressure means in the form of slip resistant foot pedal 57 is affixed to forward extremities 23 by means of paired arms 62 which engage pivot pins 63. Pressure upon the foot pedal secures the device firmly in position upon the tested surface. When downward pressure is exerted upon front handle 48, rear extreities 24 of the rails and touch rod 55 are lifted from the surface being tested. When downward pressure is applied to rear handle 49, rear extremity 24 is lowered until feet 53 make simultaneous contact with surface 10. At this point, sliderfeet 15 make simultaneous contact with surface 10, thereby lifting weight 11 slightly clear of the bottom retaining shoulder 26 and allowing unencumbered movement within rails 22. When this contact is made, touch rod 55 reaches its closed position and thereby energizes motor 36, beginning the forward pulling of drag weight 11 by propulsion bar 38, reciprocating linkage 45, and plunger 21. The drag feet 15 are simultaneously dragged across surface 10, creating frictional resistance. Limit switch 43 stops the forward motion of drag weight 11 when contacted by propulsion bar 38 at the forwardmost extremity of the stroke. The COF reading may be taken from display scale 20 of gage 17. Upon completion of the test, DPDT switch is thrown to the return position which thereby returns the drag weight until limit switch 42 is activated by propulsion bar 38.

Beveled inner surfaces 30 of lower retaining shoulder 26 center the drag weight when the device is lifted by handles 65, thereby aligning the drag weight for consistently unencumbered linear motion upon activation. A securement pin 61 penetrates rail 22 and enters a channel within weight 11, thereby securing the drag sled during transportation of the instrument.

While particular examples of the present invention have been shown and described, it is apparent that changes and modifications may be made therein without departing from the invention in its broadest aspects. The aim of the appended claims, therefore, is to cover all such changes and modifications as fall within the true spirit and scope of the invention.

Having thus described my invention, what is claimed is:

1. An improved Horizontal Pull Slipmeter having a sled assembly comprised of:
   (a) a drag weight having top and bottom surfaces and opposed sides,
   (b) downwardly directed slider feet emergent from said bottom surface, and adapted to simultaneously contact a flat surface whose coefficient of friction is to be measured, and
   (c) a force gage affixed to said drag weight and having a visual display scale and a forwardly directedactivating plunger, said improvement comprised of:
   (a) a pair of horizntally disposed elongated parallel guide means having forward and rear extremities and upper and lower retaining shoulders which define facing channels adapted to slidably embrace the opposed sides of said drag weight, premitting said sled assembly horizontally reciprocating unencumbered movement along said guide means,
   (b) a servo assembly comprising:
      (1) a housing having front, rear, upper and lower surfaces and opposed sides, said housing being attached to the forward extremities of said guide means,
      (2) an electric motor coupled to transmission means having a rearwardly directed threaded output shaft which rotates at a constant speed,
      (3) a propulsion bar coextensive with said output shaft, extending through the rear surface of said housing and terminating in a free rear extremity, said propulsion bar being threadably engaged with said output shaft so as to undergo reciprocal axial motion,
      (4) a battery power source to energize said motor,
      (5) means for controlling the rotational speed of said motor,
      (6) forward and rear limiting switches adapted to limit the length of stroke of said propulsion bar in said reciprocal movement, and
      (7) a DPDT switch adapted to control the direction of rotation of said output shaft,
   (c) a linkage having first and second extremities, said first extremity pivotably engaging the free rear extremity of said propulsion bar, said second extremity pivotably engaging the activating plunger of the force gage,
   (d) forward and rear lifting means, each comprised of paired opposed upright support arms having upper and lower extremities, said upper extremities associated with handles oriented traversely to the guide means,
   (e) four fixed support feet disposed in a substantially rectangular array and adapted to simultaneously rest upon said flat surface, and
   (f) an activation switch associated with the rear extremity of at least one of said guide means, said switch having a downwardly directed touch rod whose bottom extremity extends lower than said support feet, whereby said touch rod contacts said flat surface simultaneously with the slider feet, causing the propulsion bar to begin forward movement of the sled assembly while the servo assembly and guide means remain stationary.

2. The improvement of claim 1 wherein a pedal is disposed forwardly of said servo assembly and is pivotably associated with said guide means.

3. The improvement of claim 1 wherein the lower retaining shoulders of said guide means have beveled surfaces for positioning the drag weight.

* * * * *